US009687020B2

(12) United States Patent
Le-Thiesse et al.

(10) Patent No.: US 9,687,020 B2
(45) Date of Patent: Jun. 27, 2017

(54) METHOD FOR PREPARING AN AROMATIC COMPOSITION INCLUDING A COMPOUND CONTAINING TWO SOLIDS HAVING ORGANOLEPTIC PROPERTIES

(75) Inventors: Jean-Claude Le-Thiesse, Saint Etienne (FR); Jean-Claude Masson, Lyons (FR); Corine Cochennec, Voiron (FR); Olivier Giacomoni, Fontaines sur Saône (FR)

(73) Assignee: Rhodia Operations, Aubervilliers (FR)

( * ) Notice: Subject to any disclaimer, the term of this patent is extended or adjusted under 35 U.S.C. 154(b) by 604 days.

(21) Appl. No.: 14/239,570

(22) PCT Filed: Aug. 7, 2012

(86) PCT No.: PCT/EP2012/065468
§ 371 (c)(1),
(2), (4) Date: Feb. 19, 2014

(87) PCT Pub. No.: WO2013/026699
PCT Pub. Date: Feb. 28, 2013

(65) Prior Publication Data
US 2014/0220214 A1 Aug. 7, 2014

(30) Foreign Application Priority Data
Aug. 25, 2011 (FR) ...................... 11 57521

(51) Int. Cl.
*A23L 1/226* (2006.01)
*A23P 10/20* (2016.01)
*C07C 47/58* (2006.01)
*A23L 27/20* (2016.01)

(52) U.S. Cl.
CPC .............. *A23P 10/20* (2016.08); *A23L 27/20* (2016.08); *A23L 27/204* (2016.08); *C07C 47/58* (2013.01); *C07B 2200/13* (2013.01)

(58) Field of Classification Search
CPC ........ A23L 27/20; A23L 27/204; A23P 10/20; C07C 47/58; C07B 2200/13
See application file for complete search history.

(56) References Cited

U.S. PATENT DOCUMENTS

| 3,975,547 A * | 8/1976 | D'Ercole | A23L 2/39 |
| | | | 127/29 |
| 4,169,109 A * | 9/1979 | Yoshida | A24B 15/30 |
| | | | 426/534 |
| 4,301,184 A * | 11/1981 | Yoshida | A24B 15/32 |
| | | | 426/534 |
| 4,371,559 A | 2/1983 | Voisin et al. | |
| 4,402,985 A * | 9/1983 | Boden | A23G 3/36 |
| | | | 131/277 |
| 5,009,900 A | 4/1991 | Levine et al. | |
| 5,807,584 A | 9/1998 | Thiesse et al. | |
| 7,723,284 B2 * | 5/2010 | Mane | A61L 9/012 |
| | | | 424/66 |
| 2004/0018954 A1 | 1/2004 | Su et al. | |
| 2011/0230565 A1 | 9/2011 | Le-Thiesse | |
| 2013/0203863 A1 | 8/2013 | Le-Thiesse et al. | |

FOREIGN PATENT DOCUMENTS

| EP | 0077639 A2 | 4/1983 |
| EP | 0689772 A1 | 1/1996 |
| FR | 2482977 A1 | 11/1981 |
| JP | 2008214233 A | 9/2008 |
| PL | 54711 | 2/1968 |
| WO | WO 2010/046239 A1 | 4/2010 |
| WO | WO 2011/104208 A1 | 9/2011 |
| WO | WO 2013/026729 A1 | 2/2013 |

OTHER PUBLICATIONS

De Groote, M. 1921. "Vanilla Powders." The Spice Mill, pp. 312, 314.*
Fan, L.T., Chen, S.J., Watson, C.A. 1970. "Solids Mixing." Industrial and Engineering Chemistry. vol. 62, pp. 53-69.*
Heath, H.B. 1981. "Vanilla Powder, Imitation." Source Book of Flavors. AVI Publishing: Westport, CT. p. 751.*
Kumar, R., Sharma, P.K., Mishra, P.S. 2012. "A Review on the Vanillin derivatives showing various Biological activities." International Journal of PharmTech Research. vol. 4, pp. 266-279.*

(Continued)

*Primary Examiner* — Nikki H Dees
(74) *Attorney, Agent, or Firm* — Osha Liang LLP

(57) ABSTRACT

A method for preparing an aromatic pulverulent composition having a melting point Tf, comprising: i) feeding at least two pulverulent elementary solids having organoleptic properties into a mixer, whose chamber has been preheated beforehand to a temperature T lower than Tf, such solids being separately fed into the mixer; ii) mixing the pulverulent elementary solids in the mixer, in the absence of any external liquid phase, at a temperature T lower than Tf, at least one of the pulverulent elementary solids being fed into the mixer at a temperature Ti, such that the mixing occurs under isothermal conditions at a temperature set at such temperature T; and iii) recovering the aromatic pulverulent composition. This method is particularly suitable for preparing a composition essentially including a vanillin and ethylvanillin compound.

11 Claims, No Drawings

(56) References Cited

OTHER PUBLICATIONS

Shuba, R., Chen, I.-W. 2006. "The Effect of Powder Mixing Procedures on aSiAlON." J. Am. Ceram. Soc. vol. 89, pp. 1110-1113.*

Szczepanik, R. et al.—"Effect of intermolecular interactions between vanillin and ethylvanillin on the technology and aroma of food flavoring additives"; Roczniki Technologii i Chemii Zywnosci, 1969, vol. 15, pp. 87-99 (15 pages)—including Abstract in English.

Dolotko O. et al.—"Mechanically induced reactions in organic solids: liquid eutectics or solid-state processes?"; *New J. Chem.*, 2010, vol. 34, pp. 25-28, First published online Nov. 24, 2009 (4 pages).

Rothenberg, G., et al.—"Understanding Solid/Solid Organic Reactions", *J. Am. Chem. Soc.* (Aug. 16, 2001), vol. 123 (36), pp. 8701-8708 (8 pages).

Zenon, R. et al, "Food Essence with Vanilla Flavor", 1968, extract of CAPLUS database Accession No. 1969-402311, XP002533462 (2 pages).

* cited by examiner

METHOD FOR PREPARING AN AROMATIC COMPOSITION INCLUDING A COMPOUND CONTAINING TWO SOLIDS HAVING ORGANOLEPTIC PROPERTIES

The present application is a U.S. national stage entry under 35 U.S.C. §371 of International Application No. PCT/EP2012/065468 filed Aug. 7, 2012, which claims priority to French Application No. 11.57521 filed on Aug. 25, 2011, the whole content of this application being herein incorporated by reference for all purposes.

The present invention relates to the field of preparing pulverulent compositions, i.e. compositions in powder form, with organoleptic properties. More specifically, the invention relates to a process for preparing a pulverulent aromatic composition essentially comprising a compound based on at least two solids with organoleptic properties, in particular based on vanillin and ethylvanillin.

The aromatic products and compositions, which are aromatic in the sense that they have organoleptic properties, are used in numerous fields of application as flavoring and/or fragrance. In particular, these products and compositions with organoleptic properties are abundantly consumed in the food and animal industry. They also find applications in other fields such as pharmacy or perfumery. It follows that they are mass-consumption products and compositions. The organoleptic properties of a product or of a composition based on at least two products may be defined as all the characteristics perceived and evaluated by the consumer's senses. These properties play a primordial role in the perception of said products and compositions before use or consumption and in their assessment when they are consumed or used. The main elements contributing to the organoleptic quality are especially the visual aspect (shape, color, etc.), the consistency or texture, the taste, the odor and the aromas.

Given the increasing interest in organoleptic compositions in the agrifood, pharmaceutical and perfumery industries, there is great need for a simple process that can be readily exploited on an industrial scale for the manufacture of such organoleptic compositions. In particular, industrialists in the concerned sectors are seeking to manufacture organoleptic compositions that are in pulverulent form at room temperature. Now, the manufacture of such compositions is little described in the literature.

The Applicant has, however, already proposed a process for preparing a composition essentially comprising a compound based on vanillin and ethylvanillin in patent application WO 2010/046239. Said process comprises the co-crystallization of vanillin and ethylvanillin used in a vanillin/ethylvanillin mole ratio of 2, in molten medium or dissolved in a solvent which dissolves them. However, this process has the drawback of being difficult to transpose to the industrial scale since the crystallization of the compound is quite slow. The reason for this is that said compound undergoes overmelting, i.e. when the product is molten and when it is cooled below its melting point, it crystallizes with difficulty and remains in the liquid state for a long time. The time required for the crystallization is more or less random, and it is important to satisfactorily control the crystallization.

The present invention thus proposes to overcome these drawbacks, which are particularly observed in the case of a compound based on vanillin and ethylvanillin. More generally, the invention proposes a novel process for preparing a composition that is pulverulent at room temperature, with organoleptic properties. One of the objectives sought by the present invention is the provision of a process based on a procedure that is simple to perform on an industrial scale, directed especially toward avoiding intricate control of the temperature for the manufacture of a pulverulent composition, and having organoleptic properties.

Moreover, given the industrial difficulties and the financial losses brought about by the caking of food powders, this phenomenon, defined as the aggregation of particles, now being for example well known in the case of preparing a dry mix of vanillin and ethylvanillin powders, another objective sought by the present invention is the development of a process performed under conditions according to which caking is not favored, so as to obtain a pulverulent organoleptic composition whose particle size fully satisfies the expectations expressed by industrialists.

One subject of the present invention is a process for preparing a pulverulent aromatic composition having a melting point Tf, comprising:

i) the introduction into a mixer, whose chamber has been heated beforehand to a temperature T below Tf, of at least two pulverulent elementary solids with organoleptic properties, said solids being introduced separately into said mixer, ii) the mixing in said mixer, in the absence of any external liquid phase, of said solids at a temperature T below the temperature Tf, at least one of said pulverulent elementary solids being introduced into said mixer at a temperature Ti such that the mixing takes place under isothermal conditions at a temperature set at said temperature T, and iii) the recovery of said pulverulent aromatic composition.

Said step i) of the preparation process according to the invention uses at least two pulverulent elementary solids, i.e. solids in powder form, each having organoleptic properties. They are chosen such that the composition with organoleptic properties prepared according to the process of the invention is in pulverulent form at room temperature. According to the invention, room temperature is defined by a temperature range generally from 10 to 30° C., preferentially from 15 to 30° C. and more preferentially from 15 to 25° C. More particularly, said pulverulent elementary solids advantageously have a melting point of greater than or equal to 40° C. and very advantageously greater than or equal to 50° C. Said elementary solids generally have a melting point of less than 220° C. Preferably, elementary solids whose melting points are relatively similar, i.e. solids for which the difference between the melting points is not more than 50° C., preferably not more than 30° C., more preferably not more than 20° C. and even more preferably not more than 10° C., are chosen.

Preferably, said solids each having organoleptic properties consist of an odorous molecule containing at least one heteroatom chosen from nitrogen, oxygen and sulfur. Said molecules may be cyclic or acyclic, and saturated or unsaturated. These odorous molecules, used as aromas or fragrances, participate in a mechanism in which the olfactory organs are involved.

More preferably, said solids are chosen from aromatic aldehydes, aromatic ketones, aromatic acids, aromatic esters, aromatic ethers, phenols, oxygenous heterocycles, nitrogenous heterocycles, sulfureous and nitrogenous heterocycles, sulfur compounds, terpenes and musks.

Among the aromatic aldehydes, 4-hydroxybenzaldehyde, 4-hydroxy-3-methoxybenzaldehyde (vanillin), 4-hydroxy-3-ethoxybenzaldehyde (ethylvanillin), 4-acetoxy-3-methoxybenzaldehyde (vanillin acetate), 3,4-dimethoxybenzaldehyde (veratraldehyde), 2-hydroxy-4- methylbenzaldehyde (m-homosalicylaldehyde), (2E)-3-(4-methoxyphenyl)propenal and (trans-p-methoxycinnamaldehyde) are advantageously chosen.

Among the aromatic ketones, 4-(4-hydroxyphenyl) butan-2-one (frambinone), benzophenone, 1-(4-hydroxy-3-methoxy)ethanone (acetovanillone), 1-(3,4-dimethoxyphenyl)ethanone (3',4'-dimethoxyacetophenone), 4-(4-hydroxy-3-methoxyphenyl)-3-buten-2-one (vanillalacetone) and 4-methyl-2H-1,5-benzodioxepin-3(4H)-one (calone) are advantageously chosen.

Among the aromatic acids, 4-hydroxy-3-methoxybenzoic acid (vanillic acid), 2-methoxybenzoic acid (o-anisic acid), 4-methoxybenzoic acid (para-anisic acid), 3-methoxybenzoic acid (meta-anisic acid), 2-hydroxybenzoic acid (salicylic acid), 4-hydroxybenzoic acid (para-hydroxybenzoic acid), (2E)-3-phenyl-2-propenoic acid (trans-cinnamic acid), phenoxyacetic acid and 3-phenylpropionic acid (hydrocinnamic acid) are preferentially chosen.

Among the aromatic esters, methyl 4-hydroxy-3-methoxybenzoate (methyl vanillate), 2-phenylethyl 2-hydroxybenzoate (phenethyl salicylate), phenyl 2-hydroxybenzoate (phenyl salicylate), methyl 4-methoxybenzoate (methyl p-anisate) and 3,4-methylenedioxybenzyl acetate (heliotropyl acetate or piperonyl acetate) are preferentially chosen.

Among the aromatic ethers, 1,4-dimethoxybenzene (para-dimethoxybenzene, PDMB), 2-methoxy-1-(phenylmethoxy)-4-(1-propenyl)benzene (benzylisoeugenol) and 1-ethoxy-2-hydroxy-4-propenylbenzene (propenylguetol) are preferentially chosen.

Among the phenols, (4-hydroxy-3-methoxyphenyl) methanol (vanillyl alcohol), 4-hydroxyphenylmethanol (4-hydroxybenzyl alcohol) and 1,3-dihydroxybenzene are preferentially chosen.

Among the oxygenous heterocycles, 3-hydroxy-2-methyl-4-pyrone, 3-hydroxy-2-methyl-gamma-pyrone (maltol), 2-ethyl-3-hydroxy-4H-pyran-4-one (ethyl maltol), 1,2-benzopyrone (coumarin), 4-hydroxy-5-methyl-3(2H)-furanone (59) (norfuranol), 4,6-dimethyl-2H-pyran-2-one (levistamel) and (−)-dodecahydrotetramethylnaphthofuran (ambroxane) are preferentially chosen.

Among the nitrogenous heterocycles, 2,6-dimethylpyrazine, 2-acetylpyrazine (acetylpyrazine), 2,3,5,6-tetramethylpyrazine (tetramethylpyrazine) and 1,4-diazabenzene (pyrazine) are preferentially chosen.

Among the sulfureous compounds, diphenyl disulfide, dibenzyl disulfide and dicyclohexyl disulfide are preferentially chosen.

Among the terpenes, (1R,2S,5R)-5-methyl-2-(propan-2-yl)cyclohexanol or [(−)-menthol], (αR,1R,2R,4aS,8aS)-α-ethenyldecahydro-2-hydroxy-α,2,5,5,8a-pentamethyl-1-naphthalenepropanol or [(−)-sclareol], (1R,4S,4aS,6R,8aS)-octahydro-4,8a,9,9-tetramethyl-1,6-methanonaphthalen-1 (2H)-ol or (−)-patchouli alcohol or [(−)-patchoulol] are preferentially chosen.

Among the musks, synthetic musks such as 3,4,6,7,8-hexahydro-4,6,6,7,8,8-hexamethylcyclopenta(g)-2-benzopyran (galaxolide), cyclopentadecanone (exaltone), 6-acetyl-1,1,2,4,4,7-hexamethyltetralin (tonalide) and acetyldinitrobutylxylene (musk ketone) are preferentially chosen.

According to a first particular embodiment of the process according to the invention, each of said elementary solids is chosen from the same chemical family chosen from the families consisting of aromatic aldehydes, aromatic ketones, aromatic acids, aromatic esters, aromatic ethers, phenols, oxygenous heterocycles, nitrogenous heterocycles, sulfureous and nitrogenous heterocycles, sulfur compounds, terpenes and musks. The compounds that are preferred for performing said first particular mode and that belong to said families are those already described above.

In accordance with said first mode, each of said solids preferentially belongs to the family of aromatic aldehydes. Preferably, one of the elementary solids is vanillin and the other elementary solid is ethylvanillin. It is recalled that vanillin corresponds to the molecule having the formula 4-hydroxy-3-methoxybenzaldehyde and that ethylvanillin corresponds to the molecule having the formula 4-hydroxy-3-ethoxybenzaldehyde. Vanillin is very often associated with ethylvanillin since the presence of a small amount of ethylvanillin makes it possible to enhance the perfuming and/or organoleptic properties of vanillin. The vanillin and ethylvanillin advantageously used in the process according to the invention may have been produced via any chemical synthesis, irrespective of the starting substrate. The vanillin may also have been produced via a biochemical process, in particular a microbiological fermentation process, especially of ferulic acid.

According to a second particular embodiment of the process according to the invention, each of said elementary solids belongs to a different chemical family chosen from the families consisting of aromatic aldehydes, aromatic ketones, aromatic acids, aromatic esters, aromatic ethers, phenols, oxygenous heterocycles, nitrogenous heterocycles, sulfureous and nitrogenous heterocycles, sulfur compounds, terpenes and musks. The compounds that are preferred for performing said second particular mode and that belong to said families are those already described above.

In accordance with said second mode, at least one of the elementary solids preferentially belongs to the family of aromatic aldehydes, aromatic ethers or oxygenous heterocycles. More preferably, one of the elementary solids belongs to the family of aromatic aldehydes and the other elementary solid belongs to the family of aromatic ethers. For example, one of the elementary solids is vanillin and the other elementary solid is propenylguetol. Another advantageous combination in accordance with said second mode consists in choosing one of the elementary solids from aromatic ethers, for example para-dimethoxybenzene, and the other elementary solid from oxygenous heterocycles, for example coumarin.

Preferably, at least one of said pulverulent elementary solids is crystalline and even more preferably said two pulverulent elementary solids are crystalline.

According to a third particular embodiment of the process according to the invention, said process is performed in the presence of at least three pulverulent elementary solids each having organoleptic properties. Preferably, each of said three solids is chosen from aromatic aldehydes, aromatic ketones, aromatic acids, aromatic esters, aromatic ethers, phenols, oxygenous heterocycles, nitrogenous heterocycles, sulfureous and nitrogenous heterocycles, sulfur compounds, terpenes and musks.

In accordance with the invention, said elementary solids are introduced into the mixer in any mole ratio that is suitable for preparing said aromatic pulverulent composition obtained according to the process of the invention.

According to the particular embodiment of the process of the invention which consists in preparing a pulverulent aromatic composition essentially comprising a compound based on vanillin and ethylvanillin, the vanillin and the ethylvanillin are introduced into said mixer in a vanillin/ethylvanillin mole ratio at least equal to 2, preferentially between 2 and 3 and very preferentially between 2 and 2.6.

According to this particular embodiment of the invention, the vanillin and the ethylvanillin are advantageously introduced into said mixer in the following proportions:

from 65% to 90%, preferably from 65% to 80%, more preferably from 65% to 75% and even more preferably from 67% to 70% by weight of vanillin, from 10% to 35%, preferably from 20% to 35%, more preferably from 25% to 35% and even more preferably from 30% to 33% by weight of ethylvanillin.

In accordance with said step i) of the process according to the invention, said pulverulent elementary solids are introduced separately, i.e. each in pure substance form, into said mixer. Said solids may be introduced simultaneously or one after the other in any order. Each of said solids may or may not be introduced gradually. Prior to the introduction of said solids, the chamber of said mixer is heated to a temperature T below the melting point of the elementary solid that has the lowest melting point, said solid being chosen from said elementary solids used in the process according to the invention. Said temperature T is below the melting onset temperature of the aromatic composition prepared according to the process of the invention.

According to a particular embodiment of the process of the invention which consists in preparing an aromatic composition essentially comprising a compound based on vanillin and ethylvanillin, the chamber of said mixer is heated to a temperature T advantageously between 48 and 53° C. and very advantageously between 51 and 52° C.

Said steps i) and ii) of the process according to the invention are performed in a mixer. This is advantageously a ploughshare mixer, a paddle mixer or a band mixer, these mixers being well known to a person skilled in the art who is well-versed in the field of mixing powders. Said mixer is advantageously equipped with a jacket so as to ensure the various heat transfers by circulation of a heat-transfer fluid, advantageously water, in the jacket. The heat-transfer fluid is maintained at a temperature above or equal to the temperature T inside the chamber of said mixer. For example, the heat-transfer fluid is maintained at a temperature from 1 to 5° C. above said temperature T.

Said two pulverulent elementary solids with organoleptic properties are introduced separately into said mixer and are then mixed therein according to said step ii) of the process according to the invention.

In accordance with the process according to the invention, at least one of said pulverulent elementary solids is preheated to a temperature Ti before being introduced into said mixer, said temperature Ti being in the region of said temperature T at which the mixing according to said step ii) is performed.

Preferably, said two pulverulent elementary solids are introduced at a temperature Ti; said two solids may be preheated and introduced into said mixture at the same temperature Ti or at a slightly different temperature Ti. More precisely, said temperature Ti is advantageously chosen such that $T-20°\,C. \leq Ti \leq T+20°\,C$. According to the particular embodiment of the process of the invention which consists in preparing a pulverulent aromatic composition essentially comprising a compound based on vanillin and ethylvanillin, the vanillin and the ethylvanillin are preheated to a temperature of between 50 and 65° C., preferably to a temperature of between 55 and 62° C. and even more preferably between 58 and 61° C.

In accordance with said step ii) of the process according to the invention, the mixing of said pulverulent elementary solids with organoleptic properties is performed under isothermal conditions, i.e. at a constant temperature, equal to the temperature T to which the mixer chamber has been heated, from the start of introduction of said solids into said mixer. The preheating of at least one of said two pulverulent elementary solids to a temperature Ti as defined above, preferentially of both said pulverulent elementary solids, allows mixing at isothermal temperature in said mixer. The mixing is naturally performed in the solid phase. Said mixer is advantageously subjected to stirring. Preferably, the stirring conditions are chosen such that there is no substantial shear. Thus, a slow stirring speed is preferred. As a guide, it may be pointed out that in the case of a ploughshare mixer, the stirring conditions advantageously range between 0.2 and 1.5 m/s at the end of the paddles.

The mixer is advantageously placed under an inert atmosphere throughout the implementation of the process according to the invention. In particular, steps i) and ii) of the process according to the invention are advantageously performed under an inert atmosphere, preferentially under nitrogen. More advantageously, said steps i) and ii) are performed under an atmosphere of wet nitrogen or of dry nitrogen. Wetting of the nitrogen stream is advantageously achieved by sparging the nitrogen in water. The stream of inert gas, preferentially nitrogen, is advantageously heated to a temperature equal to $T \pm 10°\,C.$, the temperature T being that to which the mixer chamber is heated. The amount of water present in the nitrogen represents, for example, 1% to 5% by weight relative to the weight of the nitrogen, and preferably from 2% to 3% by weight relative to the weight of the nitrogen. The term "dry nitrogen" means a nitrogen stream comprising less than 0.5 g and preferably less than 0.3 g of water per kg of nitrogen.

A preferred embodiment of said step ii) of the process according to the invention consists in performing said mixing of said solids under a humid atmosphere. The humidity is provided, for example, by a stream of dry vapor, a stream of wet nitrogen, or by supplying liquid water into said mixer.

The mixing of said elementary solids with organoleptic properties in accordance with said step ii) of the process according to the invention leads to the transformation of said solids into said aromatic composition, which is recovered in accordance with said step iii) of the process according to the invention. Said step ii) is performed for a sufficient time so as to obtain transformation, preferentially total transformation, of the solids into said aromatic composition. This time is variable and especially depends on the elementary solids used and on the stirring. For example, for a mixture of vanillin and of ethylvanillin, said step ii) is advantageously performed for a time of from 30 minutes to 2 hours.

Said aromatic composition is recovered before or after cooling. The cooling of said composition obtained, performed inside or outside said mixer, is carried out at a temperature below 40° C. and preferably below 35° C. The lower limit of the cooling temperature is advantageously room temperature. Said composition is advantageously left to cool naturally inside or outside said mixer. According to a particular embodiment, the composition is left to cool in said mixer with stirring and under an inert atmosphere, down to a temperature below 40° C. and preferably down to a temperature below 35° C.

The process according to the invention advantageously comprises the introduction of at least one excipient during the implementation of said step ii) and/or the mixing of at least one excipient with said composition recovered after said step iii). Said excipient may be introduced, totally or partly, during the implementation of said step ii) and/or mixed, totally or partly, with said composition recovered after said step iii). In other words, the total amount of the excipient(s) may be introduced during the implementation of said step ii) of the process according to the invention or alternatively may be added, for example by dry mixing, to said composition recovered after said step iii) of the process according to the invention. It is also possible to fractionate the amounts of excipient(s) used such that a first part of the excipient(s) is introduced during said step ii) and the remaining part is added, preferentially by dry mixing, to said composition recovered after the implementation of said step iii).

Preferably, the total amount of the excipient(s) is introduced during the implementation of said step ii). More particularly, the total amount of said excipient(s) is introduced, preferentially at room temperature, into said mixer heated to said temperature T. It is advantageous, in a first stage, to mix said solids in said mixer and then to introduce said excipient(s) therein, preferentially with stirring.

Another preferred mode of introduction of at least one excipient into said pulverulent composition consists in mixing, at least partly, one or more excipient(s) with said composition obtained after said step iii) of the process according to the invention. Said mixing operation is advantageously performed after cooling of said composition. More particularly, mixing is performed dry, preferentially at room temperature, in a mixer, for example a ploughshare mixer, a paddle mixer or a band mixer.

The choice of the excipient(s) should take into account the intended use of the final product incorporating said composition prepared according to the process of the invention and thus have the property of being edible if it is used in the food sector. The amount of excipient(s) may be very variable and may represent from 0.1% to 90% of the weight of the final mixture. It is advantageously chosen between 20% and 70% by weight. It may be pointed out, by way of example, that from 5% to 50% by weight of an excipient may be added during said step ii) of the process according to the invention, followed by addition of a further 5% to 50% by weight of said excipient to said composition, which has preferentially been cooled, recovered after said step iii) of the process according to the invention. It is also possible to modulate the types of introduction according to the excipients, i.e. to introduce the total amount of one excipient, for example, during the implementation of said step ii) and to fractionate the amount added of another excipient, or vice versa.

It goes without saying that the same excipient may be added fractionally, i.e. during the implementation of said step ii) and then after the implementation of said step iii), or that excipients of different nature may also be introduced during the implementation of said step ii) and/or after the implementation of said step iii).

Examples of excipients that may be used in the process according to the invention are given below, and are given without any limiting nature. More preferably, said excipient is chosen from fatty substances, fatty alcohols, sugars, polysaccharides, silica, vanillin and ethylvanillin.

A first type of excipients are fatty substances. Examples that may be mentioned include fatty acids optionally in the form of salts or esters.

The fatty acids used are generally long-chain saturated fatty acids, i.e. having a chain length of between 9 and 21 carbon atoms, for instance capric acid, lauric acid, tridecylic acid, myristic acid, palmitic acid, stearic acid or behenic acid. It is possible for said acids to be in salified form, and mention may be made especially of calcium or magnesium stearate.

Fatty acid esters that may be mentioned in particular include glyceryl stearate, isopropyl palmitate, cetyl palmitate and isopropyl myristate. Mention may also be made more specifically of long-chain fatty acid esters of glycerol such as glyceryl monostearate, glyceryl monopalmitostearate, glyceryl palmitostearate, ethylene glycol palmitostearate, polyglyceryl palmitostearate, polyglycol 1500 and 6000 palmitostearate, glyceryl monolinoleate; long-chain fatty acid esters of optionally mono- or diacetylated glycerol such as monoacetyl or diacetyl monoglycerides and a mixture thereof; semisynthetic glycerides.

A fatty alcohol whose carbon atom chain is between about 16 and 22 carbon atoms may also be added, for instance myristyl alcohol, palmityl alcohol or stearyl alcohol. It is also possible to use polyoxyethylenated fatty alcohols resulting from the condensation of ethylene oxide in a proportion of from 6 to 20 mol of ethylene oxide per mole, linear or branched fatty alcohols containing from 10 to 20 carbon atoms, for instance coconut alcohol, tridecanol or myristyl alcohol.

Among the fatty substances, mention may also be made of waxes such as microcrystalline waxes, white wax, carnauba wax and paraffin.

Another type of excipients are sugars. Examples that may be mentioned include glucose, sucrose, fructose, galactose, ribose, maltose, sorbitol, mannitol, xylitol, lactitol and maltitol. Inverted sugars such as glucose syrups (in solid form) are also advantageously chosen as excipients, as are sucroglycerides derived from fatty oils such as coconut oil, palm oil, hydrogenated palm oil and hydrogenated soybean oil. Fatty acid sucroesters such as sucrose monopalmitate, sucrose monodistearate and sucrose distearate are also advantageously chosen as excipients.

Examples of other excipients that may be mentioned include polysaccharides, and mention may be made, inter alia, of the following products and mixtures thereof:
  starch is derived especially from wheat, corn, barley, rice, cassava or potato, in native, pregelatinized or modified form and more particularly native corn starches rich in amylose, pregelatinized corn starches, modified corn starches, modified waxy corn starches, pregelatinized waxy corn starches and modified waxy corn starches, in particular the starch OSSA/sodium octenylsuccinate,
  starch hydrolysates,
  dextrins and maltodextrins resulting from the hydrolysis of a starch (for example wheat or corn starch) or of a tuber starch (potato starch), and also β-cyclodextrins,
  cellulose, ethers thereof, especially methylcellulose, ethylcellulose, methylethylcellulose or hydroxypropylcellulose; or esters thereof, especially carboxymethylcellulose or carboxyethylcellulose, optionally in sodium form,
  gums such as kappa-carrageenan or iota-carrageenan gum, pectin, guar gum, locust bean gum and xanthan gum, alginates, gum arabic, acacia gum and agar-agar.

A maltodextrin with a degree of hydrolysis, measured as the "dextrose equivalent" or DE, of less than 20, preferably between 5 and 19 and more preferentially between 6 and 15 is preferentially chosen.

Other excipients that may be mentioned include flours, especially (native or pregel) wheat flour; tuber starches, more particularly potato starch, canna starch, corn starch, maizena, sago or tapioca.

An excipient that may also be used is gelatin (preferably having a gel force measured using a gelometer of 100, 175 and 250 Bloom). It may originate either from the acidic treatment of pigskin and ossein, or from the alkaline treatment of bovine skin and ossein.

In order to adjust the aromatic power of the mixture or to enhance its taste, the use of ethylmaltol and/or propenylguetol may be envisioned. The invention does not exclude the addition of a further amount of vanillin or of ethylvanillin.

The choice of excipients is made, as mentioned previously, as a function of the intended use.

The composition prepared according to the process of the invention results from the transformation of at least the two said elementary solids used in said process into a defined compound. The composition prepared according to the process of the invention is an aromatic composition, i.e. it has organoleptic properties. Said aromatic composition does not necessarily comprise an aromatic nucleus or group in the chemical sense, its organoleptic properties being sufficient in themselves for said composition to be used as a flavoring, especially a food flavoring, and/or as a fragrance.

The composition prepared according to the process of the invention is a pulverulent composition, i.e. it is in powder form. Said powder obtained after the preparation process according to the invention consists of particles and/or granules, the granules having a size generally greater than that of the particles. The size of said particles and/or granules ranges, for example, between 200 µm and 10 000 µm and preferably between 500 µm and 1000 µm. In order for the size of the particles and granules to be compatible with the intended use, a milling operation may be envisioned. It is performed such that the particle size expressed by the median diameter ($d_{50}$) ranges from 200 µm to 1000 µm and is preferably between 500 µm and 800 µm. The median diameter is defined as being such that 50% by weight of the particles have a diameter greater or less than the median diameter. The milling operation may be performed in standard apparatus such as a paddle mill, a pin mill or a hammer mill.

The composition prepared according to the process of the invention is also characterized by its melting point, noted Tf, which is different from each of the melting points of each of said elementary solids used in the process according to the invention and lower than the lowest of the melting points of the solids used in the process according to the invention.

Preferably, said composition has a melting point Tf of greater than or equal to 30° C. and preferably greater than or equal to 40° C.

Preferably, said composition prepared according to the process of the invention is a crystalline composition. It is advantageously characterized by an X-ray diffraction spectrum that is intrinsic thereto having lines for 2θ angles different from those presented by the lines featured in each of the X-ray diffraction spectra of the elementary solids from which said composition prepared according to the process of the invention is derived.

Preferably, said composition prepared according to the process of the invention is a composition essentially comprising a compound based on vanillin and on ethylvanillin. In the present text, the term "composition essentially comprising a compound based on vanillin and ethylvanillin" means a composition comprising at least 80% by weight of a mixture of a vanillin/ethylvanillin compound with a vanillin/ethylvanillin mole ratio of 2 and of vanillin: the vanillin representing less than 20% by weight of said mixture.

The characteristics of said vanillin/ethylvanillin compound have already been the subject of patent application WO 2010/046239.

Said compound is in the form of a white powder with a melting point measured by differential calorimetric analysis of 60° C.±2° C. different from that of vanillin and of ethylvanillin, respectively, of 81° C.±1° C. and 76° C.±1° C. It has an X-ray diffraction spectrum which is specific thereto and which is different from that of vanillin and of ethylvanillin. The spectrum of said compound of vanillin and of ethylvanillin especially reveals the presence of lines at angles 2θ(°)=20.7-25.6-27.5-28.0; said lines being absent from the x-ray diffraction spectra of vanillin and of ethylvanillin. Another characteristic of said compound lies in its stability: its X-ray diffraction spectrum does not undergo any significant change after prolonged storage. The change of its spectrum was monitored as a function of the storage time at room temperature: over a prolonged storage period (5 months), rigorously no change in the spectrum of said compound is observed. An absence of change of the lines specific to said vanillin/ethylvanillin compound with a vanillin/ethylvanillin mole ratio of 2 is observed. Another characteristic of said compound is that it is a compound that is non-hygroscopic or very sparingly hygroscopic, like vanillin and ethylvanillin. The hygroscopicity of said compound is determined by measuring its variation in mass after having been kept for 1 hour at 40° C. in air at 80% relative humidity. Said compound adsorbs less than 0.5% by weight of water, its content preferably being between 0.1% and 0.3% by weight of water. Said compound remains perfectly solid. Moreover, this compound has good organoleptic properties and has high aromatic power, markedly higher than that of vanillin.

Very preferably, the composition obtained according to the process of the invention comprises at least 80% by weight and preferably at least 90% by weight of a mixture of the vanillin/ethylvanillin compound and of vanillin. The composition obtained comprises less than 20% by weight and preferably less than 10% by weight of other crystalline phases of the vanillin/ethylvanillin and optionally of the vanillin phase diagram.

Said composition prepared according to the process of the invention and essentially comprising a compound based on vanillin and ethylvanillin has flowability properties such that the caking index after 24 hours of storage at 40° C. in air at 80% relative humidity under a normal stress of 2400 Pa ranges between 0.05 and 0.6.

The process according to the invention is an advantageous process that is alternative to the processes already known and used by the Applicant. In particular, the implementation of the mixing of the elementary solids, in powder form, under isothermal conditions, i.e. at a constant temperature, in accordance with said step ii) of the process according to the invention makes it possible to provide a simplified process in which the preheating of at least one of said two elementary solids, preferably said two elementary solids, avoids the installation of intricate temperature programming within the mixer. This results in numerous advantages and in particular facilitated temperature regulation for keeping the temperature of the heat-exchange fluid constant, the absence of any risk of melting of the mixture during the implementation of said step ii), and improved productivity since the elementary solids are introduced at the desired temperature as soon as they are mixed. Furthermore, the process according to the invention leads to the preparation of a composition which generally directly has the desired particle size. In particular, when performed under a dry nitrogen atmosphere, the process according to the invention leads to the preparation of a composition in the form of particles generally directly having the desired size without the need to perform milling.

Furthermore, the aromatic composition prepared according to the process of the invention, in particular the composition essentially comprising a compound based on vanillin and ethylvanillin, has improved flowability properties and absence of caking on storage.

The composition prepared according to the process of the invention may be used in many fields of application. It is very advantageously used as a flavoring in the human and animal nutrition field, in pharmacy, and as a fragrance in the cosmetics, perfumery and detergency industries.

A preferred field of application of the implementation of the composition prepared according to the process of the invention is that of biscuit and patisserie confectionery, and more particularly:
- dry biscuits: sweet biscuits of standard type, rich-tea biscuits, flat cakes, snack biscuits, shortbread biscuits, industrial patisserie: ladyfinger biscuits, cat's tongue biscuits, sponge finger biscuits, sponge cake, genoise sponge cake, madeleines, pound cake, cakes, almond-based patisserie, petits-fours.

The fundamental elements present in the mixtures intended for the abovementioned industries are protein (gluten) and starch, which are usually provided by wheat flour. For the preparation of the various types of biscuits and cakes, ingredients such as sucrose, salt, eggs, milk, fat, optionally chemical raising agents (sodium bicarbonate or other artificial raising agents) or biological yeasts and various cereal flours, etc., are added to the flour.

The incorporation of the composition prepared according to the process of the invention is performed during the manufacture, as a function of the desired product, and is carried out according to the standard techniques of the field under consideration (cf. especially J. L. Kiger and J. C. Kiger—Techniques Modernes de la Biscuiterie, Pâtisserie-Boulangerie industrielles et artisanales, Dunod, Paris, 1968, Volume 2, pp. 231 et seq.). Preferentially, the composition prepared according to the process of the invention is introduced into the fat incorporated into the preparation of the batter. As a guide, it will be pointed out that the composition prepared according to the process of the invention is introduced in an amount of from 0.005 to 0.2 g per kg of batter. The composition prepared according to the process of the invention is entirely suitable for use in the field of chocolate confectionery, irrespective of the form of implementation: chocolate bars, chocolate covering, chocolate filling. It may be introduced during the conching, i.e. the blending of the cocoa paste with the various ingredients, especially the flavorings, or after conching, by using it in cocoa butter. In this field of application, the composition prepared according to the process of the invention is used according to the type of chocolate, in a proportion of from 0.0005 g to 0.1 g per 1 kg of finished product: the highest contents being found in chocolate for covering.

Another use of the composition prepared according to the process of the invention is the manufacture of sweet confectionery of any type: sugar-coated candy, caramels, nougats, boiled sweets, fondant candy and the like.

The amount of composition prepared according to the process of the invention introduced into the products containing it depends on the more or less pronounced taste that is desired. Thus, the doses used may range between 0.001% and 0.2% by weight of the product in which said composition is present. The contents of said composition to be used are generally low, of the order of 0.02 g per 1 kg of finished product.

The composition prepared according to the process of the invention is suitable for uses in the dairy industry and more particularly in flavored and gelled milks, entremets, yoghurts, ices and ice creams.

Flavoring is performed by simple addition of the composition prepared according to the process of the invention, into one of the mixing stages required during the production of the product containing said composition.

In the case where the composition prepared according to the process of the invention is a composition essentially comprising a compound based on vanillin/ethylvanillin, another application of the composition prepared according to the process of the invention in the food sector is the preparation of vanilla-flavored sugar, i.e. the impregnation of sugar with said composition, in a content of about 7 g expressed relative to 1 kg of finished product.

The composition prepared according to the process of the invention may also be incorporated into various drinks, and mention may be made, inter alia, of grenadine and chocolate-flavored drinks. In particular, it may be used in preparations for instant drinks dispensed by automatic drink dispensers, flavored powdered drinks or chocolate powder, or alternatively in instant preparations in powder form intended for making desserts of any type, flans, cake batter or pancakes, after dilution with water or milk.

It is common practice to use vanillin for denaturing butter. To this end, the composition prepared according to the process of the invention, when said composition is a composition essentially comprising a compound based on vanillin/ethylvanillin, may be used in a proportion of 6 g per ton of butter.

Another field of application of the composition prepared according to the process of the invention is that of animal nutrition, especially for the preparation of meal for calf and pig feed. The recommended content is about 0.2 g per kg of meal to be flavored.

The composition prepared according to the process of the invention may find other applications, such as a masking agent for the pharmaceutical industry (masking the odor of a medicament) or for other industrial products (such as gum, plastic, rubber, etc.).

It is entirely suitable in totally different fields such as cosmetics and the fragrancing or detergency industry.

It may be used in cosmetics such as creams, milks, face powders and other products and also, as fragrancing ingredients, in fragrancing compositions and fragranced substances and products. The term "fragrancing compositions" denotes mixtures of various ingredients such as solvents, solid or liquid supports, fixing agents, various odorous compounds, etc., into which is incorporated the composition prepared according to the process of the invention, which is used to give various types of finished product the desired fragrance. Perfume bases constitute preferred examples of fragrancing compositions in which the composition prepared according to the process of the invention may advantageously be used in a content of from 0.1% to 2.5% by weight. The perfume bases may serve for the preparation of numerous fragranced products, for instance eaux de toilette, perfumes, aftershave lotions; toiletry and hygiene products such as bath or shower gels, deodorant or antiperspirant products, whether in the form of sticks or lotions, talcs or powders of any nature; hair products such as shampoos and haircare products of any type. Another example of the use of the composition prepared according to the process of the invention is the field of soapmaking. It may be used in a content of from 0.3% to 0.75% of the total mass to be fragranced. Generally, it is combined in this application with benjoin resinoid and sodium hyposulfite (2%).

The composition prepared according to the process of the invention may find many other applications, especially in ambient air deodorizers or any maintenance product.

The physicochemical characteristics of the compositions prepared according to the process of the invention are determined according to the following methods:

1. Melting point or melting temperature.

The melting point or melting temperature of the composition prepared according to the process of the invention is measured by differential calorimetric analysis.

The measurement is performed using a Mettler DSC822e differential analyzer under the following conditions:
   preparation of the sample at room temperature: weighing out and placing in a sample holder,
   sample holder: crimped aluminum capsule,
   sample size: 5 to 10 mg (specifically 8.4 mg in the examples below),
   temperature increase rate: 2-10° C./min,
   study range: 10-90° C.

The sample of the composition placed in the capsule is weighed out, and is crimped and then placed in the machine.

The temperature program is initiated and the melting profile is obtained on a thermogram.

The melting point is defined from a thermogram produced under the preceding operating conditions.

The onset temperature is noted: temperature corresponding to the maximum slope of the melting peak.

2. X-ray diffraction spectrum.

The X-ray diffraction spectrum of the composition prepared according to the process of the invention is determined using a PANalytical X'Pert Pro MPD machine equipped with an X' Celerator detector, under the following conditions:
   Start Position [°2Th.]: 1.5124
   End Position [°2Th.]: 49.9794
   Step Size [°2Th.]: 0.0170
   Scan Step Time [s]: 41.0051
   Anode Material: Cu
   K-Alpha1 [Å]: 1.54060
   Generator Settings: 30 mA, 40 kV 3. Flowability property and caking index. This property is particularly studied in the case of a composition based on a vanillin/ethylvanillin mixture.

The composition prepared according to the process of the invention has the characteristic of caking less on storage, which is demonstrated by the determination of the flowability index of the powder.

The flowability of powders is a technical notion that is well known to those skilled in the art. For further details, reference may be made especially to the publication "Standard shear testing technique for particulate solids using the Jenike shear cell", published by "The Institution of Chemicals Engineers", 1989 (ISBN: 0 85295 232 5).

The flowability index measurement is performed in the following manner.

The flowability of the powders is measured by shearing a sample in an annular cell (sold by D. Schulze, Germany).

The preshearing of the powders is performed under a normal stress of 5200 Pa.

The shear points needed for the locus plot for the flow of the sample are obtained for 4 normal stresses below the preshearing stress, typically 480 Pa, 850 Pa, 2050 Pa and 3020 Pa.

From the Mohr circles in the diagram of the "shear stress as a function of the normal stresses", two stresses which characterize the sample are determined on the flow locus:
   the normal stress in the main direction; this is given by the end of the large Mohr circle which passes through the presheering point,
   the cohesion force; this is given by the end of the small Mohr circle which is tangential to the flow locus and passes through the origin.

The ratio between the normal stress in the main direction and the cohesion force is a dimensionless number known as "i, the flowability index".

These measurements are taken directly after filling the annular cell, and the instant flowability index is thus obtained.

Another series of measurements is performed with a cell which has been stored for 24 hours at 40° C. and 80% relative humidity under a normal stress of 2400 Pa.

The caking index is thus obtained.

Examples illustrating the present invention are given below, with no limiting nature.

EXAMPLE 1

2100 g of vanillin (VA) powder and 900 g of ethylvanillin (EVA) powder are heated at 60° C. overnight in an oven. The VA/EVA mass ratio is 70/30. The humidity of these powders is 0.1% by weight.

A ploughshare mixer equipped with a 15 liter tank heated via a jacket is preheated to 51° C. The jacket is fed with water thermostatically maintained at 52° C.

A circulation of wet nitrogen is established in the mixer at a flow rate of 200 l/h. Humidification of the nitrogen stream is ensured by sparging it through water maintained at 40° C. so as to obtain 25 g of water per kg of nitrogen. The feed line between the water bath and the mixer is maintained at 45° C. so as to avoid any condensation in the pipes.

After preheating the mixer to 51° C., the preheated vanillin is introduced into said mixer and the preheated ethylvanillin is then introduced therein. The mixer stirrer is switched on at a speed of 100 rpm, i.e. a speed at the end of the paddles of 1.25 m/s for 5 minutes. The stirring is then reduced to a speed of 40 rpm (i.e. a speed of 0.5 m/s at the end of the paddles) and is maintained for 1 hour. The heating of the water feeding the jacket is then stopped and, by natural cooling, the temperature of the product is brought to 35° C. The mixer stirring and the nitrogen circulation are stopped and the mixer is emptied. The product is then recovered.

The product is screened through 1 mm; the undersize (particles with a size of less than 1 mm) represents 56% by weight of the total mass. The 1 mm oversize (granules with a size of greater than 1 mm) is milled using a Quadro Comill mill equipped with a 1 mm grate. The two fractions are then combined and the mixture is homogenized to give the pulverulent composition with organoleptic properties.

The melting point of the composition obtained is determined by differential calorimetric analysis as described previously. The thermogram obtained has a main peak which corresponds to the vanillin/ethylvanillin compound. The melting point (Tonset), which corresponds to the maximum slope of the peak, is 59.5° C.

The X-ray diffraction spectrum of the composition has characteristic lines at angles 2θ=20.7-25.6-27.5-28.0 as illustrated in figure 1 and which differentiate it from the spectra of vanillin and of ethylvanillin.

The flowability index and the caking index, measured as described previously using an annular cell, are, respectively, 9.6 and 0.14.

EXAMPLE 2

2000 g of the composition, obtained in example 1, after the screening operation are mixed with 3000 g of Glucidex®

IT12 (maltodextrin) sold by Roquette. The mixing is performed at room temperature in a ploughshare mixer for a time of 5 minutes. The flowability index and the caking index, measured as described previously using an annular cell, are, respectively, 15 and 0.56. The X-ray diffraction spectrum of the composition thus obtained as a mixture with an excipient based on maltodextrin has characteristic lines at angles $2\theta=20.7$-$25.6$-$27.5$-$28.0$.

EXAMPLE 3

1400 g of vanillin (VA) powder and 600 g of ethylvanillin (EVA) powder are heated at 60° C. overnight in an oven. The VA/EVA mass ratio is 70/30. The humidity of these powders is 0.1% by weight.

A ploughshare mixer equipped with a 15 liter tank heated via a jacket is preheated to 52° C. The jacket is fed with water thermostatically maintained at 52° C. The mixer is placed under an inert atmosphere provided by flushing with dry nitrogen (40 l/h). After preheating the mixer to 52° C., the preheated vanillin is introduced into said mixer and the preheated ethylvanillin is then introduced therein. The mixer stirrer is switched on at a speed of 100 rpm, i.e. a speed at the end of the paddles of 1.25 m/s, for 5 minutes. The stirring is then reduced to a speed of 40 rpm and is maintained for 1 hour.

3 kg of Glucidex® IT12 sold by Roquette (maltodextrin) are then added, at room temperature, to the mixer containing the VA-EVA mixture in which the transformation at 52° C. takes place, to obtain the desired composition. The jacket temperature is maintained at T=52° C. and the mixture is stirred at 100 rpm for 5 minutes. Heating of the water feeding the jacket is then stopped, and the mixer stirring and the nitrogen circulation are stopped. The mixer is emptied and the product is then recovered and cooled naturally in the ambient air.

The particle size of the product is checked by screening: the size of the particles (equivalent diameter) forming the product thus obtained is less than 1 mm. No milling operation is necessary. The melting point of the product obtained is determined by differential calorimetric analysis as described previously. The thermogram obtained has a main peak which corresponds to the vanillin/ethylvanillin compound. The melting point (Tonset), which corresponds to the maximum slope of the peak, is 58.5° C.

The X-ray diffraction spectrum of the particles has characteristic lines at angles $2\theta=20.7$-$25.6$-$27.5$-$28.0$. The flowability index and the caking index, measured as described previously using an annular cell, are, respectively, 13 and 0.58.

The invention claimed is:

1. A process for preparing a pulverulent aromatic composition having a melting point Tf, comprising:
   i) introducing into a mixer, whose chamber has been heated beforehand to a temperature T lower than Tf, wherein T is of between 48 and 53° C., at least two pulverulent elementary solids with organoleptic properties, wherein one of said pulverulent elementary solids is vanillin, and the other pulverulent elementary solid is ethylvanillin, said pulverulent elementary solids being introduced separately into said mixer,
   ii) mixing in said mixer, in the absence of any external liquid phase, said pulverulent elementary solids at a temperature T lower than Tf, at least one of said pulverulent elementary solids being introduced into said mixer at a temperature Ti such that the mixing takes place under isothermal conditions at a temperature set at said temperature T, and
   iii) recovering said pulverulent aromatic composition.

2. The preparation process as claimed in claim 1, wherein said pulverulent elementary solids have a melting point greater than or equal to 40° C.

3. The preparation process as claimed in claim 1, wherein said at least two pulverulent elementary solids are introduced at said temperature Ti, said temperature Ti being chosen such that $T-20°$ C.$\leq Ti \leq T+20°$ C. in said step (ii).

4. The preparation process as claimed in claim 1, wherein the vanillin and the ethylvanillin are preheated to a temperature of between 50 and 65° C.

5. The preparation process as claimed in claim 1, wherein said steps i) and ii) are performed under an atmosphere of wet nitrogen or of dry nitrogen.

6. The preparation process as claimed in claim 1, further comprising at least one step selected from the group consisting of:
   introducing at least one excipient during the implementation of said step ii); and mixing at least one excipient with said pulverulent aromatic composition recovered after said step iii).

7. The preparation process as claimed in claim 6, wherein the total amount of said at least one excipient is introduced at room temperature into said mixer heated to said temperature T.

8. The preparation process as claimed in claim 6, wherein said at least one excipient is selected from the group consisting of fatty substances, fatty alcohols, sugars, polysaccharides, silica, vanillin, and ethylvanillin.

9. The preparation process as claimed in claim 1, wherein said pulverulent aromatic composition has a melting point Tf greater than or equal to 30° C.

10. The preparation process as claimed in claim 1, wherein the mixing of said solids in step ii) is performed under a humid atmosphere.

11. The preparation process as claimed in claim 10, wherein a gas stream sparged through liquid water is supplied to said mixer to provide said humid atmosphere.

* * * * *